(12) United States Patent
Rao et al.

(10) Patent No.: US 8,633,234 B2
(45) Date of Patent: Jan. 21, 2014

(54) RIFAXIMIN

(75) Inventors: Dharmaraj Ramachandra Rao, Maharashtra (IN); Rajendra Narayanrao Kankan, Maharashtra (IN); Manjinder Singh Phull, Maharashtra (IN); Maruti Ghagare, Maharashtra (IN)

(73) Assignee: Cipla Limited, Mumbai, IN (US)

(*) Notice: Subject to any disclaimer, the term of this patent is extended or adjusted under 35 U.S.C. 154(b) by 770 days.

(21) Appl. No.: 12/441,368

(22) PCT Filed: Sep. 24, 2007

(86) PCT No.: PCT/GB2007/003629
§ 371 (c)(1),
(2), (4) Date: Aug. 3, 2009

(87) PCT Pub. No.: WO2008/035109
PCT Pub. Date: Mar. 27, 2008

(65) Prior Publication Data
US 2009/0312357 A1 Dec. 17, 2009

(30) Foreign Application Priority Data
Sep. 22, 2006 (IN) .......................... 1520/MUM/2006

(51) Int. Cl.
*C07D 498/22* (2006.01)

(52) U.S. Cl.
USPC .......................... 514/393; 540/456

(58) Field of Classification Search
USPC .......................... 540/456; 514/393
See application file for complete search history.

(56) References Cited

U.S. PATENT DOCUMENTS

| | | | |
|---|---|---|---|
| 3,089,818 A | 5/1963 | Stone | |
| 4,341,785 A | 7/1982 | Marchi et al. | |
| 4,557,866 A | 12/1985 | Cannata et al. | |
| 7,045,620 B2 | 5/2006 | Viscomi et al. | |
| 7,709,634 B2 * | 5/2010 | Kothakonda et al. | 540/456 |
| 2005/0272754 A1 | 12/2005 | Viscomi et al. | |

FOREIGN PATENT DOCUMENTS

| | | |
|---|---|---|
| CA | 1215976 | 12/1986 |
| EP | 0161534 A2 | 11/1985 |
| EP | 1698630 A1 | 9/2006 |
| WO | 99/04823 A1 | 2/1999 |
| WO | 02/32459 A2 | 4/2002 |
| WO | 2007/047253 A2 | 4/2007 |
| WO | 2008/035109 A1 | 3/2008 |
| WO | 2009/137672 A1 | 11/2009 |
| WO | 2010/067072 A1 | 6/2010 |

OTHER PUBLICATIONS

Foreign communication from the priority application—International Search Report and Written Opinion, PCT/ GB2007/003629, Jan. 3, 2008, 12 pages.
Foreign communication from the priority application—International Preliminary Report on Patentability, PCT/ GB2007/003629, Dec. 17, 2008, 11 pages.
Foreign communication from a related counterpart application—International Search Report and Written Opinion, PCT/ GB2009/002854, Feb. 24, 2010, 12 pages.
Foreign communication from a related application—International Preliminary Report on Patentability, PCT/ GB2009/002854, Jun. 14, 2011, 12 pages.
Patent application entitled "Rifaximin Complexes," by Maruti Ghagare, et al., filed Jul. 8, 2011 as U.S. Appl. No. 13/132,054.
Office Action dated Feb. 24, 2012, (7 pages), U.S. Appl. No. 13/350,623, filed Jan. 13, 2012.
Patent application entitled entitled "Rifaximin," by Dharmaraj Ramachandra Rao, et al., filed Jan. 13, 2012 as U.S. Appl. No. 13/350,623.

* cited by examiner

*Primary Examiner* — Bruck Kifle
(74) *Attorney, Agent, or Firm* — Novak Druce Connolly Bove + Quigg LLP; Janelle D. Waack

(57) ABSTRACT

Amorphous rifaximin, methods of making it, and pharmaceutical compositions containing it. Also described are methods of converting amorphous rifaximin to crystalline rifaximin and vice versa.

1 Claim, 3 Drawing Sheets

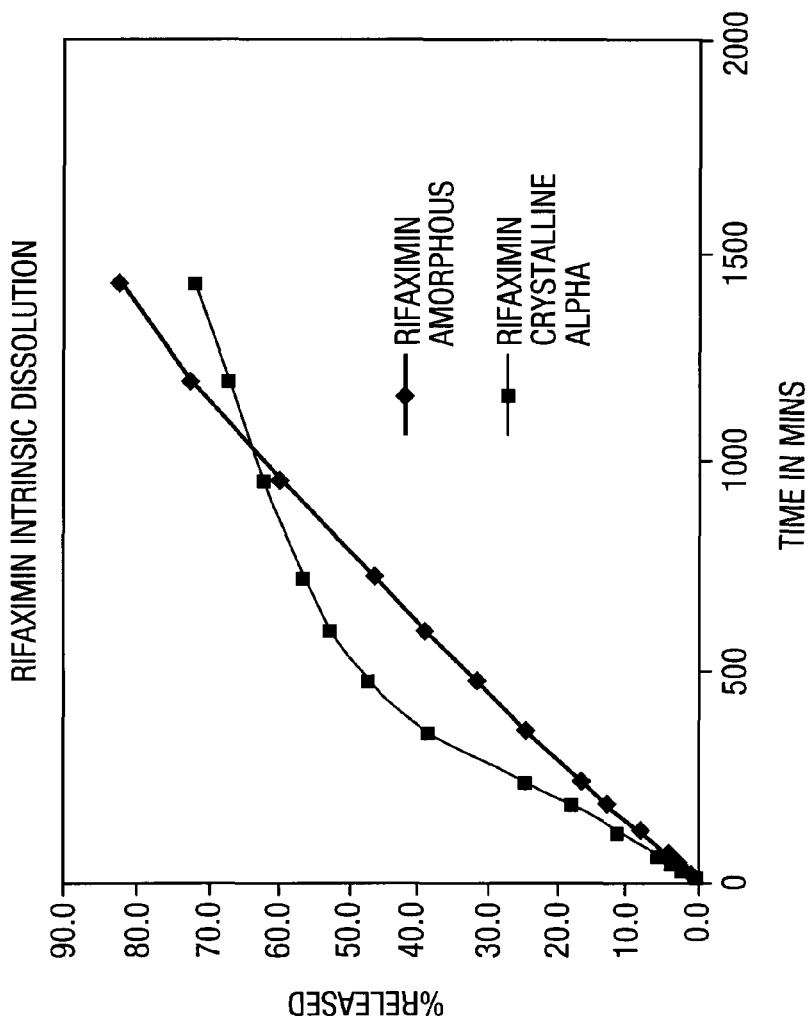

RIFAXIMIN

CROSS-REFERENCE TO RELATED APPLICATIONS

This application is a filing under 35 U.S.C. 371 of International Application No. PCT/GB2007/003629 filed Sep. 24, 2007, entitled "Rifaximin," claiming priority of Indian Patent Application No. 1520/MUM/2006 filed Sep. 22, 2006, which applications are incorporated by reference herein in their entirety.

FIELD OF THE INVENTION

The present invention relates to amorphous rifaximin, pharmaceutical compositions containing the same, processes for preparing amorphous rifaximin and to therapeutic uses and therapeutic methods of treatment employing amorphous rifaximin, or such pharmaceutical compositions, medicaments or products.

BACKGROUND OF THE INVENTION

Rifaximin is a semi-synthetic, rifamycin-based non-systematic antibiotic. It is chemically termed as (2S,16Z,18E,20S,21S,22R,23R,24R,25S,26S,27S,28E)-5,6,21,23,25-pentahydroxy-27-methoxy-2,4,11,16,20,22,24,26-octamethyl-2,7-(epoxypentadeca-[1,11,13]trienimino) benzofuro[4,5-e]pyrido[1,2-a]-benzimida-zole-1,15(2H)-dione,25-acetate (I).

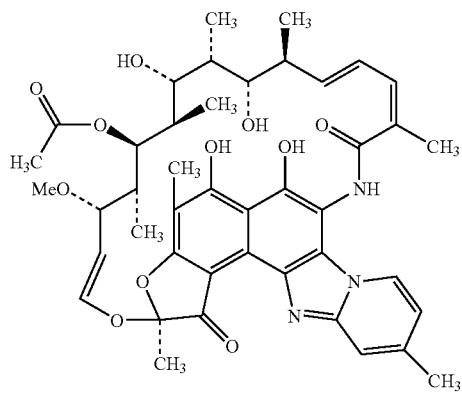

(I)

Rifaximin is used for treatment of travelers' diarrhea caused by noninvasive strains of *Escherichia coli*.

Rifaximin was first disclosed in U.S. Pat. No. 4,341,785 which also discloses a process for its preparation and a method for crystallization of rifaximin using suitable solvents or mixture of solvents. However, this patent does not mention the polymorphism of rifaximin.

Canadian patent CA1215976 discloses a process for the synthesis of imidazo rifamycins which comprises reacting rifamycin S with 2-amino-4-methylpyridine.

U.S. Pat. No. 4,557,866 discloses a process for preparation of rifaximin, but does not mention the polymorphs of rifaximin.

U.S. Pat. No. 7,045,620 discloses crystalline polymorphic forms of rifaximin which are termed as rifaximin α, rifaximin β and rifaximin γ. These polymorphic forms are characterized using X-ray powder diffraction. Further this patent mentions that γ form is poorly crystalline with a high content of amorphous component. This patent also discloses processes for preparation of these polymorphs which involve use of processes of crystallization and drying as disclosed in U.S. Pat. No. 4,557,866 along with control of temperature at which the product is crystallized, drying process, water content thereof. Further, according to this patent, crystal formation depends upon the presence of water within the crystallization solvent.

The above patent discloses rifaximin α which is characterized by water content lower than 4.5% & powder X-ray diffractogram having significant peaks are at values of diffraction angles 2θ of 6.6°; 7.4°; 7.9°, 8.8°, 10.5°, 11.1°, 11.8°, 12.9°, 17.6°, 18.5°, 19.7°, 21.0°, 21.4°, 22.1°; rifaximin β which is characterized by water content higher than 4.5% & powder X-ray diffractogram having significant peaks are at values of diffraction angles 2θ of 5.4°; 6.4°; 7.0°, 7.8°, 9.0°, 10.4°, 13.1°, 14.4°, 17.1°, 17.9°, 18.3°, 20.9° and rifaximin γ which is characterized by poorer powder X-ray diffractogram because of poor crystallinity. The significant peaks are at values of diffraction angles 2θ of 5.0°; 7.1°; 8.4°.

US2005/0272754 also discloses polymorphs of rifaximin namely rifaximin α form, rifaximin β form & rifaximin γ form characterized by powder X-ray diffractogram, intrinsic dissolution rates and processes of preparation of polymorphic forms of rifaximin. However, none of the above patents disclose a wholly amorphous form of rifaximin.

It is a well known fact that different polymorphic forms of the same drug may have substantial differences in certain pharmaceutically important properties. The amorphous form of a drug may exhibit different dissolution characteristics and in some case different bioavailability patterns compared to crystalline forms.

Further, amorphous and crystalline forms of a drug may have different handling properties, dissolution rates, solubility, and stability.

Furthermore, different physical forms may have different particle size, hardness and glass transition temperatures. Amorphous materials do not exhibit the three-dimensional long-range orders found in crystalline materials, but are structurally more similar to liquids where the arrangement of molecules is random.

Amorphous solids do not give a definitive x-ray diffraction pattern (XRD). In addition, amorphous solids do not give rise to a specific melting point and tend to liquefy at some point beyond the glass transition temperature. Because amorphous solids do not have lattice energy, they usually dissolve in a solvent more rapidly and consequently may provide enhanced bioavailability characteristics such as a higher rate and extent of absorption of the compound from the gastrointestinal tract. Also, amorphous forms of a drug may offer significant advantages over crystalline forms of the same drug in the manufacturing process of solid dosage form such as compressibility.

Consequently, it would be a significant contribution to the art to provide an amorphous form of rifaximin having increased solubility, and methods of preparation, pharmaceutical formulations, and methods of use thereof.

OBJECTIVES OF THE INVENTION

Therefore, it is an object of the invention to provide amorphous form of rifaximin and a process for preparation thereof.

It is also an object of the invention to provide processes for the inter-conversion of amorphous rifaximin to crystalline rifaximin and the inter-conversion of the crystalline forms.

Another object of the present invention is to provide pharmaceutical compositions comprising an amorphous form of rifaximin.

Yet another object of the present invention is to provide therapeutic uses and therapeutic methods of treatment employing compositions comprising amorphous rifaximin.

SUMMARY OF THE INVENTION

In one aspect, the invention provides amorphous form of rifaximin. This may be characterized by its powder X-ray diffraction pattern, as shown in FIG. 1. The amorphous rifaximin may be characterised by its FT-IR spectrum, as shown in FIG. 2.

In another aspect, the invention provides a process for preparation of amorphous form of rifaximin.

In another aspect, the invention provides processes for inter-conversion of amorphous rifaximin to crystalline rifaximin and inter-conversions of crystalline forms.

In another aspect, the invention comprises pharmaceutical compositions comprising amorphous form of rifaximin along with pharmaceutically acceptable carrier.

In another aspect, the present invention provides therapeutic uses and therapeutic methods of treatment employing the compositions comprising amorphous rifaximin.

The present invention provides amorphous rifaximin in bulk form, unlike the prior art which discloses a mixture of amorphous and crystalline rifaximin, and which provides no disclosure as to how to prepare bulk amorphous rifaximin. The amorphous rifaximin is substantially pure with polymorphic purity of 99% or more. Furthermore, it is substantially free of any peaks of crystalline rifaximin.

In accordance with the invention, it is possible to obtain amorphous rifaximin which is substantially free of any crystalline rifaximin.

BRIEF DESCRIPTION OF THE DRAWINGS

FIG. 3 is a graphical representation of intrinsic dissolution of amorphous rifaximin compared with the α Form of rifaximin

DETAILED DESCRIPTION OF THE INVENTION

The term room temperature used in present application refers to a temperature range between 25-30° C.

The term stripping in this application refers to removal of traces of the first solvent from residue by adding second solvent and distilling it to residue.

Figure 1:
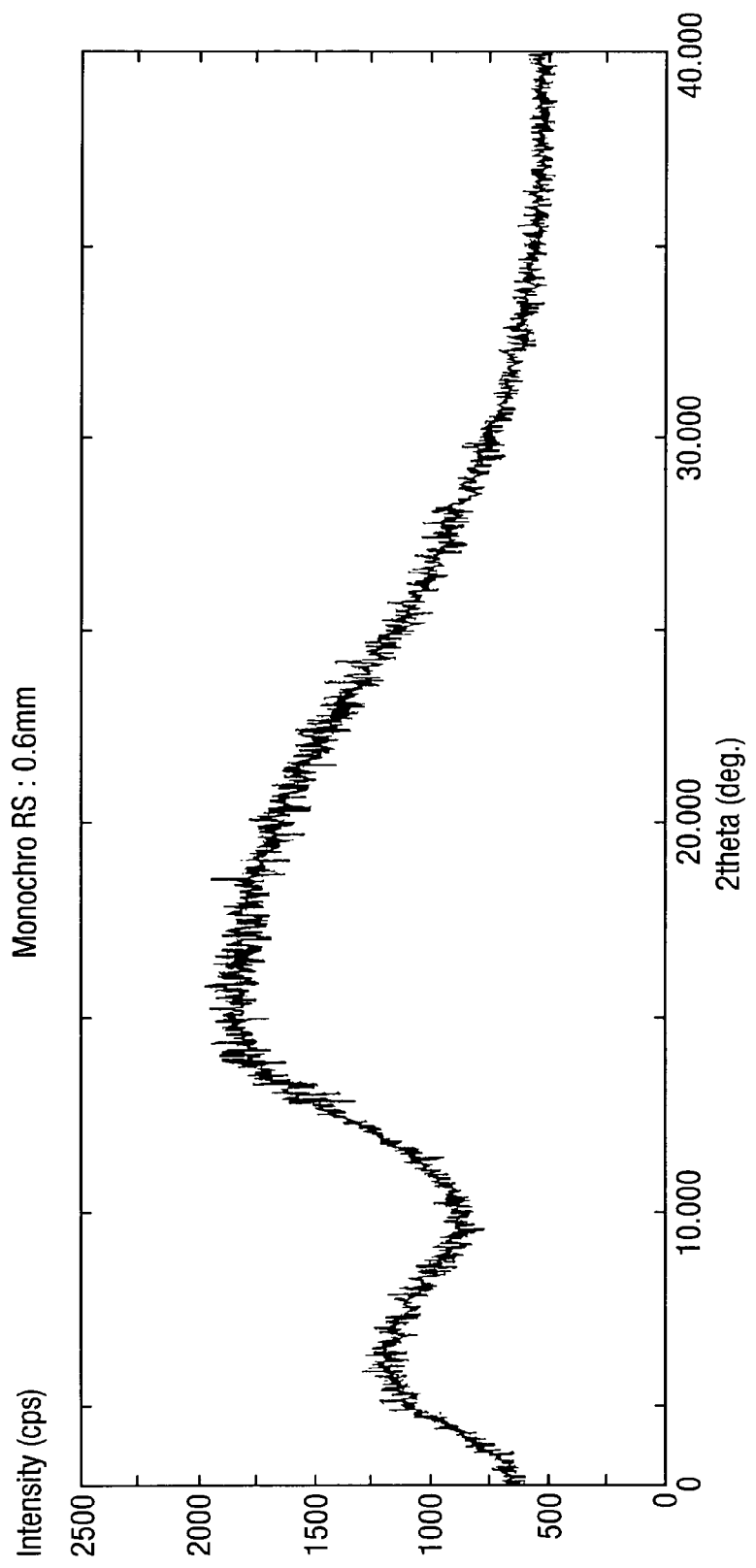
FIG. 1 is an X-ray powder diffractogram (XRD) of amorphous rifaximin made in accordance with example 1 as described below.
Figure 2:
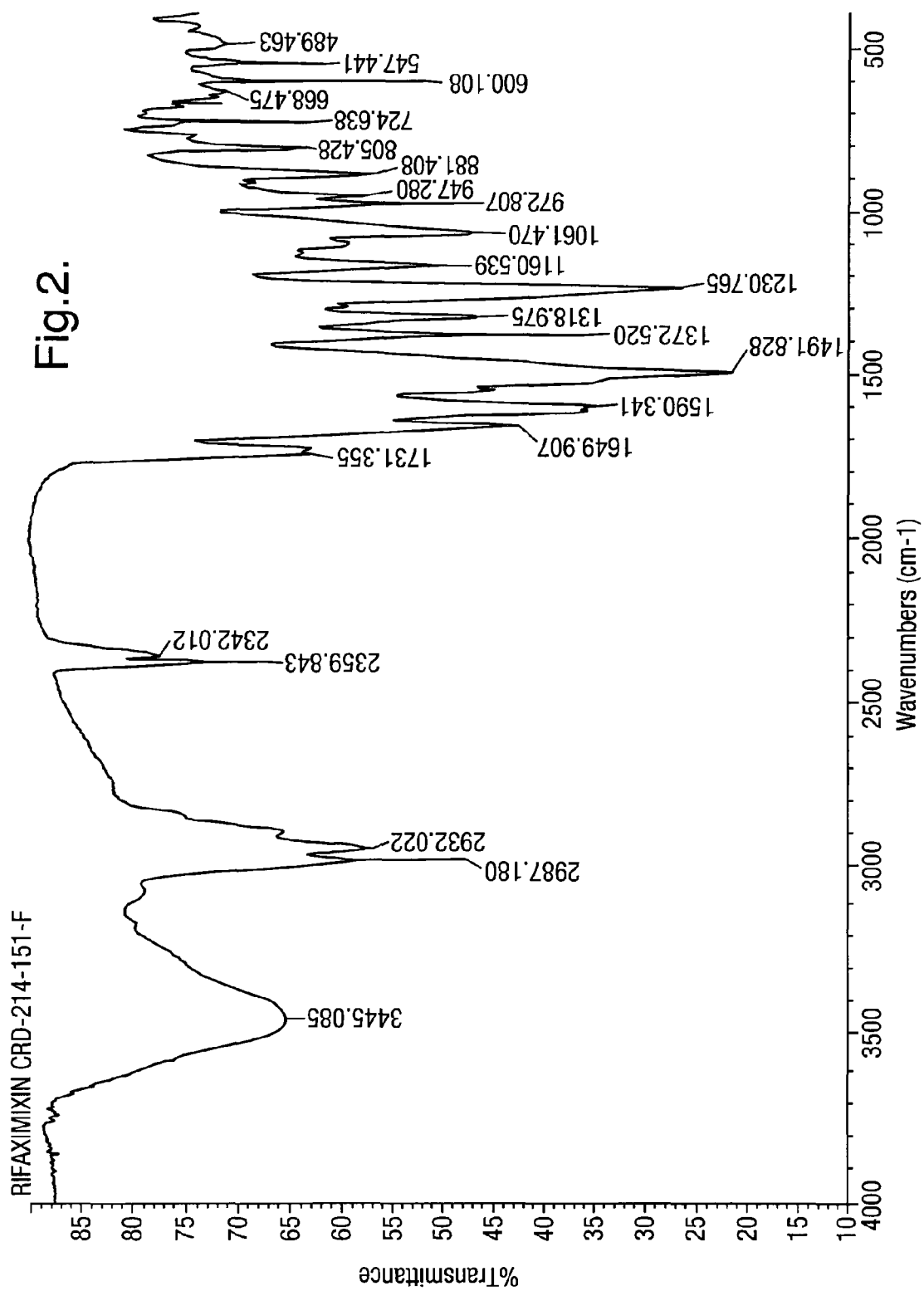
FIG. 2 is an FT-IR spectrum of amorphous rifaximin, made in accordance with example 1 described below.

In one embodiment, the present invention provides amorphous form of rifaximin. Amorphous form of rifaximin of the present invention is characterized by its powder X-ray diffraction pattern. The XRPD of the amorphous rifaximin was measured on a Rigaku DMAX 2200 Ultima+ PC series X-ray powder diffractometer using a Cu $K_\alpha$ radiation source, and is characterized by its XRPD pattern as shown in FIG. 1. The amorphous rifaximin can be characterised by its FT-IR pattern, as shown in FIG. 2. Amorphous rifaximin according to the present invention is conveniently prepared by a process, which comprises reaction of Rifamycin S with 2-amino-4-picoline in presence of a suitable solvent like dichloromethane, ethyl acetate, dichloroethylene, chloroform, in an inert atmosphere. All these solvents can be used alone or in mixture among them or with water in various ratios.

Further, iodine dissolved in suitable solvent like dichloromethane, ethyl acetate, dichloroethylene, chloroform, is added at room temperature to the above reaction mixture and then stirred. Further, suitable reducing agent dissolved in water, is preferably added to the above reaction mass and stirred at room temperature and then cooled to 10-15° C.

The reducing agent used preferably comprises at least one of ascorbic acid, isoascorbic acid, sulphur dioxide, dihydroxyacetone.

Further, pH of the reaction mass is adjusted between 1.5-2.5, preferably to 2.0-2.2 under stirring. The reaction mass is preferably further stirred for 10-15 minutes and organic layer is separated. The separated organic layer is preferably washed with water, followed by washing with 10% sodium thiosulphate or 10% sodium metabisulphite and finally washed with water till pH of the organic layer is neutral. This separated organic layer is preferably further charcoalised, filtered, dried over sodium sulphate and concentrated under vacuum below 50° C. to residue.

This residue contains rifaximin and can be further treated to obtain crystalline rifaximin (as in the prior art) or amorphous rifaximin (in accordance with the invention).

In the prior art, to manufacture the form known as the β form, the residue would be treated with a water miscible solvent, followed by drying in air at 80-110° C. To manufacture the γ form in accordance with the prior art, the residue is treated with an organic acid and water, followed by drying in air at 100-110° C. I think is is best to maintain the temperatures, if they are the working temperatures, as we cannot add the information after filing.

In accordance with the present invention, amorphous rifaximin is prepared by subjecting a residue containing rifaximin to a stripping step, followed by mixing with a mixture of water immiscible solvents, followed by drying at a temperature below 40° C.—the amorphous rifaximin may be recovered after the drying step. The drying can be carried out at the temperature somewhat below 40° C., e.g., at room temperature (for example 25° C.).

More specifically, the residue obtained is preferably stripped out to dryness with suitable water immiscible organic solvent and the material obtained is isolated by stirring with the same solvent used for stripping or a mixture of solvents, preferably at room temperature. Further, the solid is filtered, washed with same solvents and dried below 40° C. to get amorphous rifaximin.

The suitable solvent used for stripping of the product is a water immiscible organic solvent selected from n-heptane, n-hexane, di-isopropyl ether, dichloromethane, dichloroethylene, chloroform and ethyl acetate.

The schematic representation for preparation of amorphous rifaximin is as follows:

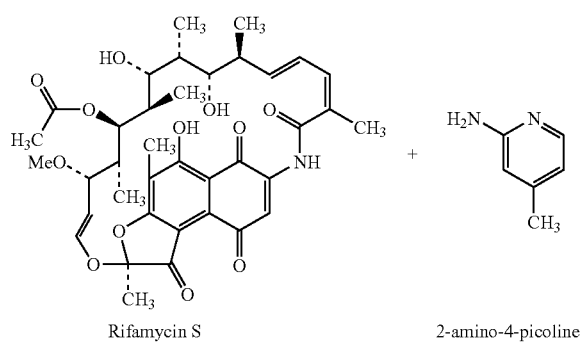

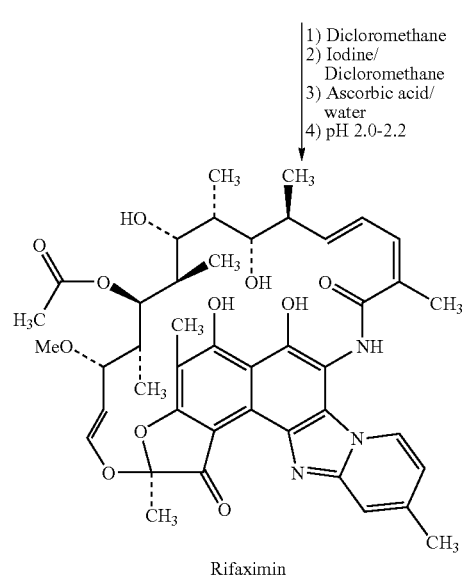

Amorphous rifaximin according to the present invention can be characterized by various parameters like solubility, intrinsic dissolution, bulk density, tapped density.

Rifaximin is known to exist in 3 polymorphic Forms namely α Form, β Form & γ Form of which the α Form is thermodynamically the most stable. Hence, the amorphous form of rifaximin was studied in comparison with α Form.

Further, when intrinsic dissolution of amorphous rifaximin is carried out against the α Form, it is observed that the amorphous rifaximin has better dissolution profile than α Form which is shown in table below (this data is also shown graphically in FIG. 3):

Dissolution medium: 1000 ml of 0.1M Sodium dihydrogen phosphate monohydrate+4.5 g of sodium lauryl sulphate.
Temperature: 37±0.5° C.
Rotation speed: 100 rpm
Particle size: Amorphous rifaximin—11 microns
α Form of rifaximin—13 microns

| Time in minutes | % Release of Amorphous Rifaximin | % Release of α Form of Rifaximin |
|---|---|---|
| 15 | 1.1 | 0.8 |
| 30 | 1.9 | 1.8 |
| 45 | 2.9 | 3.0 |
| 60 | 3.7 | 4.4 |
| 120 | 8.1 | 11.0 |
| 180 | 12.6 | 18.0 |
| 240 | 16.6 | 24.6 |
| 360 | 24.7 | 38.7 |
| 480 | 32.0 | 47.5 |
| 600 | 39.5 | 52.7 |
| 720 | 46.4 | 56.4 |
| 960 | 60.4 | 62.9 |
| 1200 | 72.9 | 67.8 |
| 1400 | 83.0 | 72.7 |

Amorphous rifaximin exhibits bulk density in the range of 0.3-0.4 g/ml and tapped density is in the range of 0.4-0.5 g/ml while the α Form rifaximin exhibits bulk density in the range of 0.2-0.3 g/ml & tapped density is in the range of 0.3-0.4 g/ml. These higher densities of amorphous rifaximin are advantageous in formulation specifically in tablet formulation, for example, it gives better compressibility.

Another aspect of the present invention is to provide conversion of amorphous rifaximin to crystalline γ form rifaximin which comprises dissolving amorphous rifaximin in an organic solvent, heating preferably to 40-60° C. and stirring the reaction mixture to get clear solution. To this organic solution, water may be added gradually preferably at 40-60° C. and stirred. The reaction mass may be cooled gradually to room temperature and stirred. The resulting solid may be filtered and washed with mixture of organic acid and water. The solid may be further washed with mixture of organic acid and water and then with water. The washed solid is dried at 100-110° C. to yield rifaximin γ form.

Preferably, the organic solvent used for dissolution and washing, is organic acid. The organic acid preferably can be acetic acid or formic acid.

Another embodiment of the present invention is to provide process for the conversion of amorphous rifaximin to crystalline β form rifaximin which comprises dissolving amorphous rifaximin in an organic solvent, heating preferably to 40-60° C. and stirring the reaction mixture to get clear solution. To this organic solution, water may be added gradually at 40-60° C. and stirred. The reaction mass may be cooled gradually to room temperature and stirred. The resulting solid may be filtered and washed with mixture of suitable organic solvent and water. The solid may be further washed with mixture of organic solvent and water and then with water. The washed solid is dried at 80-110° C. to yield rifaximin β form.

Preferably, the organic solvent used for dissolution and washing, comprises at least one of water miscible solvents preferably acetone, acetonitrile, $C_{1-4}$ alcohols.

Another embodiment of the present invention is to provide process for inter-conversion of γ form of rifaximin which comprises dissolving crystalline rifaximin in suitable solvent, heating preferably to 40-60° C. and stirred. Water is added, preferably dropwise, preferably at 40-60° C. to the above mixture under stirring. The resulting mixture may be cooled gradually to room temperature and stirred. The solid obtained may be filtered, washed with mixture of solvents. Further the above solid may be washed with water, dried at 80-110° C. to yield β form of rifaximin.

Suitable solvent used for dissolving and washing the product is selected from water miscible solvents selected from group comprising of acetone, acetonitrile, lower alcohols or mixtures thereof.

Yet another embodiment of the present invention is to provide conversion of crystalline form of rifaximin to amorphous rifaximin which comprises dissolving crystalline rifaximin in suitable solvent at room temperature and filtered. The filtrate may be washed with suitable solvent mentioned above and the solution may be concentrated, preferably under vacuum, preferably at 40-60° C. to get residue. The residue obtained is stripped out with suitable water immiscible organic solvent and then stirred in the same solvent or mixture of solvents used for dissolving at room temperature, filtered, washed with same solvent and dried below 40° C. to get amorphous rifaximin.

The suitable solvent used for dissolving and stripping the product is selected from dichloromethane, dichloroethylene, chloroform, n-heptane, n-hexane and diisopropyl ether.

Yet another aspect of present invention provides pharmaceutical composition comprising amorphous form of rifaximin in combination with a pharmaceutically acceptable carrier. In addition to active ingredient(s) the pharmaceutical composition of the present invention may contain one or more pharmaceutically acceptable ingredients.

The composition of the present invention can be formulated into variety of dosage forms, such as tablets, capsules, pills, caplets, lozenges, dispersible granules, dry powder syrup, ready to use suspension; parenteral dosage forms available in the art; various inhalation formulations; transdermal formulations, and the like. These formulations can be prepared using processes known in the art.

EXAMPLES

The present invention will now be further illustrated by the following examples, which do not limit the scope of the invention in any way.

The amorphous rifaximin according to the invention may be used as a medicament or in the manufacture of a medicament for treating bowel related disorders like irritable bowel syndrome, diarrhea, traveler's diarrhea, microbe associated diarrhea, Crohn's disease, chronic pancreatitis, pancreatic insufficiency and/or colitis. In a preferred embodiment, the invention is directed to a method of treating diarrhea, comprising administering a therapeutically effective amount of amorphous rifaximin according to the invention to a patient in need thereof.

Example 1

Rifamycin S 100 g (0.143 moles), dichloromethane 300 ml and 2-amino-4-picoline, 46.4 g (0.434 moles) were mixed at room temperature under argon atmosphere. Iodine 19 g (0.074 moles) dissolved in dichloromethane 700 ml, was added dropwise in 30-45 minutes at room temperature. Reaction mixture was then stirred at room temperature for 15-18 hours. L(−) Ascorbic acid 20 g (0.113 moles) dissolved in 100 ml water was added. The mixture was stirred for 30-45 minutes at room temperature and then cooled to 10 to 15° C. The pH of the reaction mixture was adjusted to 2 using 12.5% dil. HCl solution. The mass was stirred for 10 to 15 minutes, organic layer was separated and washed at first with demineralized water then with 10% sodium thiosulfate and finally with water till neutral pH was obtained. The organic layer was charcolized, filtered through hyflo, dried over sodium sulfate and concentrated under vacuum below 50° C. The product was stripped out with n-heptane and crude material thus obtained was stirred with a mixture of 20% dichloromethane and heptane [500 ml] at room temperature for 30-45 minutes. The solid was filtered, washed with a mixture of 20% dichloromethane and n-heptane and dried under vacuum below 40° C. for 10-12 hours to get amorphous rifaximin 100 g.

Example 2

Amorphous rifaximin (100 g) was dissolved in acetic acid (200 ml) at 50° C., stirred for 30-45 minutes and demineralized water (200 ml) was added dropwise at 50° C. in 30-45 minutes. Stirring was continued at 50° C. for 30-45 minutes, cooled gradually to room temperature and stirred for 2 hours. The solid obtained was filtered and washed at first with acetic acid-water 1:1 mixture then with 10% acetic acid-water mixture and finally washed with water. The solid obtained was dried at 100-110° C. for 12-15 hours to get 62-65 g of rifaximin-γ-form.

Example 3

Amorphous rifaximin (100 g) was dissolved in formic acid (200 ml) at 50° C., stirred for 30-45 minutes and demineralized water (200 ml) was added dropwise at 50° C. in 30-45 minutes. Stirring was continued at 50° C. for 30-45 minutes, cooled gradually to room temperature and stirred for 2 hours. The solid obtained was filtered and washed at first with formic acid-water 1:1 mixture then with 10% formic acid-water mixture and finally washed with water. The solid obtained was dissolved in Isopropyl alcohol (310 ml) at 50° C. and stirred at 50° C. for 30 minutes. Demineralized water (310 ml) was added dropwise at 50° C. in 30-45 minutes and stirring was continued at the same temperature for 30-45 minutes. The mixture was cooled gradually to room temperature and stirred for 2 hours. The solid obtained was filtered, washed with Isopropyl alcohol-water 1:1 mixture and then with demineralized water, dried at 80-90° C. for 10-15 hours to get 40-45 g of rifaximin-β-form.

Example 4

Rifaximin γ form (62 g) was dissolved in acetonitrile (310 ml) at 50° C. and stirred at 50° C. for 30 minutes. Demineralized water (310 ml) was added dropwise at 50° C. in 30-45 minutes and stirring was continued at the same temperature for 30-45 minutes. The mixture was cooled gradually to room temperature and stirred for 2 hours. The solid obtained was filtered, washed with acetonitrile-water 1:1 mixture and then with demineralized water, dried at 80-90° C. for 10-15 hours to get 40-45 g of rifaximin-β-form.

Example 5

Crystalline rifaximin (40 g) was dissolved in dichloromethane (10-15 volumes) at room temperature, filtered through hyflo and washed with dichloromethane (2 volumes). The solution was concentrated under vacuum at 50° C. The solid was stripped out with n-heptane and stirred in n-heptane (50 ml) at room temperature for 30 minutes. Finally the solid was filtered, washed with n-heptane and dried under vacuum below 40° C. to get 35-38 g of amorphous rifaximin.

Example 6

Tablet composition containing amorphous rifaximin.

| Excipient | Quantity (mg/tab) |
| --- | --- |
| Rifaximin amorphous | 200.00 |
| Colloidal silicon dioxide | 2.00 |
| Disodium edetate | 2.00 |

-continued

| Excipient | Quantity (mg/tab) |
|---|---|
| Hydroxypropyl methyl cellulose | 10.00 |
| Microcrystalline cellulose | 162.00 |
| Purified water | q.s. |
| Sodium starch glycolate | 20.00 |
| Glycerol palmitostearate | 4.00 |
| Suitable film coating | 10.00 |

A solid oral pharmaceutical formulation according to the present invention can be manufactured by granulation process known in the art.

The invention claimed is:

1. Rifaximin in an amorphous form characterized by the XRPD pattern shown in FIG. 1.

\* \* \* \* \*